(12) United States Patent
Buezo et al.

(10) Patent No.: US 7,709,522 B2
(45) Date of Patent: May 4, 2010

(54) KAPPA SELECTIVE OPIOID RECEPTOR ANTAGONIST

(75) Inventors: Nuria Diaz Buezo, Madrid (ES); Concepcion Pedregal-Tercero, Madrid (ES); David Lee McKinzie, Whitestown, IN (US); Charles Howard Mitch, Columbus, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/352,869

(22) Filed: Jan. 13, 2009

(65) Prior Publication Data
US 2009/0186873 A1    Jul. 23, 2009

(30) Foreign Application Priority Data
Jan. 22, 2008    (ES)    ................... 08380012

(51) Int. Cl.
C07D 207/06    (2006.01)
C07D 207/04    (2006.01)
A61K 31/4025    (2006.01)
A61K 31/40    (2006.01)

(52) U.S. Cl. ...................... 514/429; 548/577
(58) Field of Classification Search ................. 548/574, 548/575; 514/428
See application file for complete search history.

(56) References Cited

U.S. PATENT DOCUMENTS

| | | | |
|---|---|---|---|
| 5,457,208 | A | 10/1995 | Portoghese et al. |
| 6,528,518 | B2 | 3/2003 | Carlezon |
| 7,196,100 | B2 | 3/2007 | Benesh et al. |
| 7,288,543 | B2 | 10/2007 | Broughton et al. |
| 7,378,448 | B2 | 5/2008 | Mitch et al. |
| 7,381,719 | B2 | 6/2008 | Blanco-Pillado et al. |
| 7,381,750 | B2 | 6/2008 | De La Torre et al. |
| 7,396,943 | B2 | 7/2008 | Benesh et al. |
| 7,399,774 | B2 | 7/2008 | Siegel et al. |
| 7,414,132 | B2 | 8/2008 | De La Torre et al. |
| 7,531,557 | B2 | 5/2009 | Mitch |
| 2006/0052439 | A1 | 3/2006 | Beguin et al. |
| 2007/0155793 | A1 | 7/2007 | Benesh |
| 2007/0213394 | A1 | 9/2007 | Beguin et al. |
| 2008/0207701 | A1 | 8/2008 | Chappell et al. |
| 2008/0255152 | A1 | 10/2008 | Blanco-Pillado et al. |
| 2008/0269296 | A1 | 10/2008 | Blanco-Pillado et al. |
| 2009/0023785 | A1 | 1/2009 | Pedregal-Tercero |
| 2009/0196824 | A1 | 8/2009 | Elman et al. |

FOREIGN PATENT DOCUMENTS

| | | |
|---|---|---|
| WO | WO 02/053533 | 7/2002 |
| WO | WO 2004/026305 | 4/2004 |
| WO | WO 2007/115975 | 10/2007 |
| WO | WO 2008/021849 | 2/2008 |
| WO | WO 2008/021851 | 2/2008 |
| WO | WO 2008/032156 | 3/2008 |

OTHER PUBLICATIONS

Dolle et al. Bioorganic & Medicinal Chemistry Letters 2009, 19, 3647-3650.*
Grant et al. Arch Gen Psychiatry 2004, 61, 807-816.*
Walker, et al., "Pharmacological Evidence for a Motivational Role of κ-Opioid Systems in Ethanol Dependence," *Neuropsychopharmacology*, vol. 33, pp. 643-652 (2008).
Kovacs, et al., "Decreased Oral Self-Administration of Alcohol in κ-Opioid Receptor Knock-Out Mice," *Alcoholism: Clinical and Experimental Research*, vol. 29, No. 5, pp. 730-738 (2005).
Grant, et al., "Prevalence and Co-occurrence of Substance Use Disorders and Independent Mood and Anxiety Disorders," *Arch Gen Psychiatry*, vol. 61, pp. 807-816 (2004).
Gregg, et al., "Reasons for increased substance use in psychosis," *Clinical Psychology Review*, vol. 27, pp. 494-510 (2007).
McCann, "Potential of Buprenorphine/Naltrexone in Treating Polydrug Addiction and Co-occuring Psychiatric Disorders," *Clinical Pharmacology & Therapeutics*, vol. 83, No. 4, pp. 627-630 (2008).
"Co-Occurring Alcohol Use Disorder and Schizophrenia," http://www.athealth.com/Consumer/disorders/schizophreniaalcohol_print.html (2009).
Shippenberg, et al., "Dynorphin and the pathophysiology of drug addiction," *Pharmacology & Therapeutics*, vol. 116, pp. 306-321 (2007).
Mague, et al., "Antidepressant-Like Effects of k-Opioid Receptor Antagonists in the Forced Swim Test in Rats," *The Journal of Pharmacology and Experimental Therapeutics*, vol. 305, No. 1, pp. 323-330 (2003).
Knoll, et al., "Anxiolytic-Like Effects of κ-Opioid Receptor Antagonists in Models of Unlearned and Learned Fear in Rats," *The Journal of Pharmacology and Experimental Therapeutics*, vol. 323, No. 3, pp. 838-845 (2007).
Cornelius, et al., "Alcohol and psychiatric comorbidity," *Recent Dev. Alcohol*, vol. 16, pp. 361-374 (2003).
Schuckit, "Comorbidity between substance use disorders and psychiatric conditions,"*Addiction*, vol. 101, Suppl. 1, pp. 76-88 (2006).
Thomas, et al., Importance of Phenolic Address Groups in Opioid Kappa Receptor Selective Antagonists, *J. Med. Chem*, vol. 47, pp. 1070-1073 (2004).
Carroll, et al., "N-Substituted 4β-Methyl-5-(3-hydroxyphenyl)-7α-amidomorphans Arte Potent, Selective κ Opioid Receptor Antagonists," *J. Med. Chem.*, vol. 49, pp. 1781-1791 (2006).

(Continued)

*Primary Examiner*—Rebecca L Anderson
*Assistant Examiner*—Matthew P Coughlin
(74) *Attorney, Agent, or Firm*—John C. Demeter

(57) ABSTRACT

A selective kappa opioid receptor antagonist, (S)-3-Fluoro-4-[4-[2-(3,5-dimethylphenyl)pyrrolidin-1-yl-methyl]phenoxy]benzamide or a pharmaceutically acceptable salt thereof, useful for treating ethanol use disorder withdrawal, and anxiety and/or depression, or schizophrenia as independent comorbid conditions.

16 Claims, No Drawings

OTHER PUBLICATIONS

Thomas, et al., "Identification of (3R)-7-Hydroxy-N-((1S)-1-{[(3R,4R)-4-(3-hydroxyphenyl)-3,4-dimethyl-1-piperidinyl]methyl}-2-methylpropyl)-1,2,3,4-tetrahydro-3-isoquinolinecarboxamide as a Novel Potent and Selective Opioid κ Receptor Antagonist," *J. Med. Chem.*, vol. 46, pp. 3127-3137 (2003).

Thomas, et al., "Discovery of an Opioid κ Receptor Selective Pure Antagonist from a Library of N-Substituted 4β-Methyl-5-(3-hydroxyphenyl)morphans," *J. Med. Chem.*, vol. 45, pp. 3524-3530 (2002).

Stevens, et al., "Potent and Selective Indolomorphinan Antagonists of the Kappa-Opioid Receptor," *J. Med. Chem.*, vol. 43, pp. 2759-2769 (2000).

Portoghese, et al., "Binaltorphimine-Related Bivalent Ligands and Their κ Opioid Receptor Antagonist Selectivity," *J. Med. Chem.*, vol. 31, pp. 836-841 (1988).

Jones, et al., "5'-Guanidinonaltrindole, a highly selective and potent κ-opioid receptor antagonist," *European Journal of Pharmacology*, vol. 396, pp. 49-52 (2000).

Beardsley, et al., "Differential effects of the novel kappa opioid receptor antagonist, JDTic, on reinstatement of cocaine-seeking induced by footshock stressors vs cocaine primes and its antidepressant-like effects in rats," *Psychopharmacology*, vol. 183, pp. 118-126 (2005).

McLaughlin, et al., "κ-Opioid Receptor Antagonism and Prodynorphin Gene Disruption Block Stress-Induced Behavioral Responses," *The Journal Of Neuroscience*, vol. 23, No. 13, pp. 5674-5683 (2003).

Rothman, et al., "An open-label study of a functional opioid κ antagonist in the treatment of opioid dependence," *Journal of Substance Abuse Treatment*, vol. 18, pp. 277-281 (2000).

Written Opinion of the International Searching Authority of International Application No. PCT/US2009/030811, Mailing Date Apr. 8, 2009.

Blednov, et al., "Reduced alcohol consumption in mice lacking preprodynorphin," Alcohol, 40:73-86 (2006).

Bortolato, et al., "Kappa Opioid Receptor Activation Disrupts Prepulse Inhibition of the Acoustic Startle in Rats," Biol. Psychiatry, 57:1550-1558 (2005).

Bouwknecht, et al., "The stress-induced hyperthermia paradigm as a physiological animal model for anxiety: A review of pharmacological and genetic studies in the mouse," Neuroscience and Biobehavioral Reviews, 31:41-59 (2007).

Geyer, et al., "Pharmacological studies of prepulse inhibition models of sensorimotor gating deficits in schizophrenia: a decade in review," Psychopharmacology, 156:117-154 (2001).

Olivier, et al., "Stress-induced hyperthermia and anxiety: pharmacological validation," European Journal of Pharmacology, 463:117-132 (2003).

Petit-Demouliere, et al., "Forced swimming test in mice: a review of antidepressant activity," Psychopharmacology, 177:245-255 (2005).

Swerdlow, et al., "Neural circuit regulation of prepulse inhibition of startle in the rat: current knowledge and future challenges," Pyschopharmacology, 156:194-215 (2001).

* cited by examiner

KAPPA SELECTIVE OPIOID RECEPTOR ANTAGONIST

Ethanol use disorder is a significant and prevalent worldwide health problem and is a causal factor in serious medical conditions and behaviors, such as liver cirrhosis, liver cancer, coronary heart disease, ischemic stroke, fetal alcohol syndrome, automobile accidents and fatalities, and domestic violence.

Ethanol dependence is a chronic relapsing disorder, and relapse represents a major challenge to treatment efforts. To date, there is no therapeutic intervention that has proven to be satisfactory in preventing relapse and sustaining abstinence. There is a need for new and more effective pharmacotherapeutics that will enable patients to better control their ethanol consumption as well as battle risks for relapse.

The current pharmacological standards for treatment of ethanol dependence in humans in the United States are naltrexone (an opioid antagonist), acamprosate (a functional glutamate antagonist) and disulfiram (an aldehyde dehydrogenase inhibitor). In combination with behavioral management, these agents are approved for maintaining abstinence. Although modest efficacy is observed with these treatments, they all suffer from compliance issues, at least in part, contributing to clinical unmet need. For instance, many patients diagnosed with ethanol dependence have concurrent symptoms of anxiety and/or depression, or schizophrenia. The current treatments described above do not provide benefit for these comorbid symptoms that may play a role in subsequent ethanol use disorder relapse. The present invention provides for such an agent that will enable the patient to abstain or reduce heavy ethanol drinking and alleviate concomitant symptoms of anxiety and/or depression or schizophrenia.

Naltrexone is a mu receptor preferring opioid receptor antagonist having antagonist activity at each of the three opioid receptors, mu, kappa and delta. Clinically, naltrexone has demonstrated efficacy in maintaining ethanol abstinence and reducing ethanol craving. However, naltrexone may cause hepatotoxicity at doses exceeding 50 mg per day and appropriate monitoring is required. This hepatotoxicity is particularly concerning in a patient population with enhanced susceptibility to liver injury because of their ethanol use.

Depending on the experimental conditions, selective activation of kappa opioid receptors have been shown to either increase or decrease consumption of ethanol; the discrepancies in the literature may be related to additional pharmacological effects (e.g., dysphoria and cognitive disruption) of kappa agonists. On the other hand, selective pharmacological kappa receptor antagonism or genetic deletion of kappa receptors have been shown to decrease ethanol self-administration in animal models of alcoholism. This suggests a pharmaceutical agent that is a selective antagonist for the kappa versus mu and delta opioid receptors could fill a significant need in ethanol use disorder therapy.

There is a need for a pharmaceutical agent in ethanol use disorder therapy that evidences kappa opioid receptor antagonist selectivity. There is also a need for a pharmaceutical agent that will improve outcomes in one or more of: number of days abstinent on a per month basis; number of heavy drinking days on a per month basis; and number of drinks per drinking day over a one month basis. There is a further need in ethanol use disorder therapy for an agent that will demonstrate efficacy for one or both of anxiety and depression or schizophrenia that are frequently independent comorbid conditions in patients with ethanol use disorder.

Opioid receptor antagonists, such as those compounds in WO 2004/026305, have been disclosed.

The compound disclosed herein is a kappa opioid receptor antagonist. This compound's properties make it suitable as a therapeutic agent for facilitating ethanol use disorder withdrawal such as reducing the quantity of ethanol used at each drinking session over a defined time period; reducing the frequency of ethanol use days over a defined time period; maintaining diminished quantity and/or frequency of use over a defined time period; or abstinence from ethanol consumption over a defined time period. The compounds' properties as shown in small animal models make it suitable to treat anxiety and/or depression or schizophrenia disorders in patients having said disorder, or as an independent comorbid disorder in patients also having ethanol use disorder.

One aspect of the present invention provides:

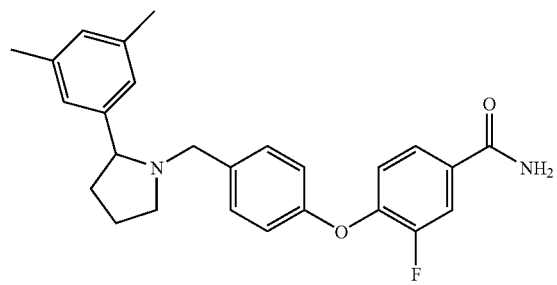

3-Fluoro-4-[4-[2-(3,5-dimethylphenyl)pyrrolidin-1-yl-methyl]phenoxy]benzamide or a pharmaceutically acceptable salt thereof.

A second aspect of the present invention provides:

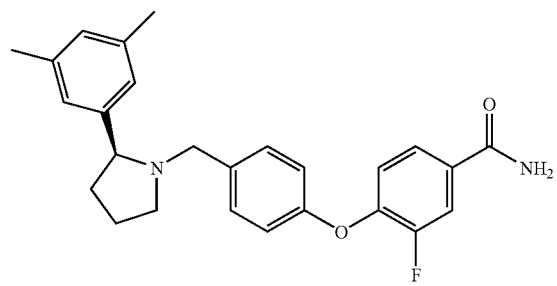

(S)-3-Fluoro-4-[4-[2-(3,5-dimethylphenyl)pyrrolidin-1-yl-methyl]phenoxy]benzamide or a pharmaceutically acceptable salt thereof.

A third aspect of the present invention provides a pharmaceutical formulation comprising 3-fluoro-4-[4-[2-(3,5-dimethylphenyl)pyrrolidin-1-yl-methyl]phenoxy]benzamide, or a pharmaceutically acceptable salt thereof, in association with a pharmaceutically acceptable carrier, diluent and/or excipient.

A fourth aspect of the present invention provides a pharmaceutical formulation comprising (S)-3-fluoro-4-[4-[2-(3,5-dimethylphenyl)pyrrolidin-1-yl-methyl]phenoxy]benzamide, or a pharmaceutically acceptable salt thereof, in association with a pharmaceutically acceptable carrier, diluent and/or excipient.

A fifth aspect of the present invention provides a method of selectively antagonizing kappa opioid receptors in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

A sixth aspect of the present invention provides a method of treating ethanol use disorder in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

A seventh aspect of the present invention provides a method of treating an anxiety disorder selected from panic disorder, obsessive-compulsive disorder, social phobia, generalized anxiety disorder, specific phobia, and posttraumatic stress disorder in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

A eighth aspect of the present invention provides a method of treating an anxiety disorder selected from panic disorder, obsessive-compulsive disorder, social phobia, generalized anxiety disorder, specific phobia, and posttraumatic stress disorder and ethanol use disorder in a patient in need thereof which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

An ninth aspect of the present invention provides a method of treating a depressive illness selected from major depression, dysthymia and bipolar disorder in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

A tenth aspect of the present invention provides a method of treating a depressive illness selected from major depression, dysthymia and bipolar disorder, and ethanol use disorder in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

An eleventh aspect of the present invention provides a method of treating an anxiety disorder selected from panic disorder, obsessive-compulsive disorder, social phobia, generalized anxiety disorder, specific phobia, and posttraumatic stress disorder and a depressive illness selected from major depression, dysthymia and bipolar disorder, in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

A twelfth aspect of the present invention provides a method of treating an anxiety disorder selected from panic disorder, obsessive-compulsive disorder, social phobia, generalized anxiety disorder, specific phobia, and posttraumatic stress disorder and a depressive illness selected from major depression, dysthymia and bipolar disorder and ethanol use disorder in a patient in need thereof, which comprises administering a therapeutically effective amount of (S)-3-fluoro-4-[4-[2-(3,5-dimethyl-phenyl)pyrrolidin-1-yl-methyl]phenoxy]benzamide, or a pharmaceutically acceptable salt thereof, to said patient.

A thirteenth aspect of the present invention provides a method of treating schizophrenia in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

A fourteenth aspect of the present invention provides a method of treating schizophrenia, and ethanol use disorder in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

A fifteenth aspect of the present invention provides a compound 3-fluoro-4-[4-[2-(3,5-dimethylphenyl)pyrrolidin-1-yl-methyl]phenoxy]benzamide or (S)-3-fluoro-4-[4-[2-(3,5-dimethylphenyl)pyrrolidin-1-yl-methyl]phenoxy] benzamide, or a pharmaceutically acceptable salt thereof, for use in therapy.

A sixteenth aspect of the present invention provides a compound 3-fluoro-4-[4-[2-(3,5-dimethylphenyl)pyrrolidin-1-yl-methyl]phenoxy]benzamide or (S)-3-fluoro-4-[4-[2-(3,5-dimethylphenyl)pyrrolidin-1-yl-methyl]phenoxy] benzamide, or a pharmaceutically acceptable salt thereof, for the use in treatment of ethanol use disorder.

A seventeenth aspect of the present invention provides a compound 3-fluoro-4-[4-[2-(3,5-dimethylphenyl)pyrrolidin-1-yl-methyl]phenoxy]benzamide or (S)-3-fluoro-4-[4-[2-(3,5-dimethylphenyl)pyrrolidin-1-yl-methyl]phenoxy]benzamide, or a pharmaceutically acceptable salt thereof, for the use in treatment of:

a) an anxiety disorder selected from panic disorder, obsessive-compulsive disorder, social phobia, generalized anxiety disorder, specific phobia, and posttraumatic stress disorder; or b) a depressive illness selected from major depression, dysthymia and bipolar disorder; or c) an anxiety disorder selected from a) and a depressive illness selected from b); or d) ethanol use disorder and an anxiety disorder selected from a); or e) ethanol use disorder and a depressive illness selected from b); or f) ethanol use disorder and an anxiety disorder selected from a) and a depressive illness selected from b); or g) schizophrenia; or h) ethanol use disorder and schizophrenia.

An eighteenth aspect of the present invention provides the use of a compound 3-fluoro-4-[4-[2-(3,5-dimethylphenyl)pyrrolidin-1-yl-methyl]phenoxy]benzamide or (S)-3-fluoro-4-[4-[2-(3,5-dimethylphenyl)pyrrolidin-1-yl-methyl]phenoxy]benzamide, or a pharmaceutically acceptable salt thereof, for the manufacture of a medicament for the treatment of ethanol use disorder.

A nineteenth aspect of the present invention provides the use of a compound 3-fluoro-4-[4-[2-(3,5-dimethylphenyl)pyrrolidin-1-yl-methyl]phenoxy]benzamide or (S)-3-fluoro-4-[4-[2-(3,5-dimethylphenyl)pyrrolidin-1-yl-methyl]phenoxy]benzamide, or a pharmaceutically acceptable salt thereof, for the manufacture of a medicament for the treatment of:

a) an anxiety disorder selected from panic disorder, obsessive-compulsive disorder, social phobia, generalized anxiety disorder, specific phobia, and posttraumatic stress disorder; or b) a depressive illness selected from major depression, dysthymia and bipolar disorder; or c) an anxiety disorder selected from a) and a depressive illness selected from b); or d) ethanol use disorder and an anxiety disorder selected from a); or e) ethanol use disorder and a depressive illness selected from b); or f) ethanol use disorder and an anxiety disorder selected from a) and a depressive illness selected from b); or g) schizophrenia; or h) ethanol use disorder and schizophrenia.

A twentieth aspect of the present invention provides a pharmaceutical composition comprising a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, and a therapeutically effective amount of a tertiary amine tricyclic norepinephrine reuptake inhibitor selected from amitriptyline, clomipramine, doxepin, imipramine and (+)-trimipramine, or a pharmaceutically acceptable salt thereof, in association with a pharmaceutically acceptable carrier, diluent and/or excipient. A preferred embodiment of this composition comprises (S)-3-fluoro-4-[4-[2-(3,5-dimethylphenyl)pyrrolidin-1-yl-methyl]phenoxy]benzamide, or a pharmaceutically acceptable salt thereof, and imipramine, or a pharmaceutically acceptable salt thereof.

A twenty-first aspect of the present invention provides the use of a compound (S)-3-fluoro-4-[4-[2-(3,5-dimethylphenyl)pyrrolidin-1-yl-methyl]phenoxy]benzamide, or a pharmaceutically acceptable salt thereof, and a tertiary amine tricyclic norepinephrine reuptake inhibitor selected from amitriptyline, clomipramine, doxepin, imipramine and (+)-trimipramine, or a pharmaceutically acceptable salt thereof, in the manufacture of a medicament for the treatment of:

a) ethanol use disorder; or b) a depressive illness selected from major depression, dysthymia and bipolar disorder; or c) ethanol use disorder and a depressive illness selected from b). A preferred embodiment of this aspect of the present invention comprises (S)-3-fluoro-4-[4-[2-(3,5-dimethylphenyl)pyrrolidin-1-yl-methyl]phenoxy]benzamide, or a pharmaceutically acceptable salt thereof, and imipramine, or a pharmaceutically acceptable salt thereof.

Selective kappa opioid receptor antagonism has been shown to decrease dependence-induced ethanol self administration in ethanol dependent Wistar rats while nondependent animals were not affected, Walker and Koob, *Neuropsychopharmacology*, advance online publication, 2 May 2007, pgs. 1-10. Similarly, mice lacking the gene that produces the kappa opioid receptor or the endogenous ligand precursor preprodynorphin, drink significantly less alcohol than do wild-type mice (Kovacs et al., Alcohol: Clin & Exp. Res. 2005, 29: 730-739; Blednov et al., Alcohol 2006, 40: 73-86).

It has been established that there is a relationship between ethanol use disorder and anxiety and/or depression disorders, as independent comorbid conditions, in the same patients. *Arch. Gen. Psychiatry*, 61, 807-816 (2004). This association points to the desirability of treating both the ethanol use disorder and the independent comorbid anxiety and/or depression disorders in patients with a single active pharmaceutical agent. It has also been established that there is a relationship between ethanol use disorder and schizophrenia, as independent comorbid conditions in the same patients. Gregg et al., *Clinical Psychology Review*, 27 494-510 (2007). This association points to the desirability of treating both the ethanol use disorder and the independent comorbid schizophrenia in patients with a single active pharmaceutical agent.

Ethanol use disorder is a cluster of cognitive, behavioral and physiological symptoms demonstrating there is a continuing use of the substance despite significant use-related problems. There is a pattern of repeated self-administration that results in tolerance, withdrawal and compulsive substance-taking behavior. The problems related to ethanol use disorder are varied. There may be repeated failure to fulfill major role obligations, repeated use in situations in which it is physically hazardous, multiple legal problems, and recurrent social and interpersonal problems. These problems occur repeatedly during the same 12-month period.

Tolerance is the need for increased amounts of ethanol to achieve the desired effect, or a diminished effect with continued use of the same amount of ethanol.

Generally, withdrawal is a behavioral change, having physiological and cognitive components, that occurs when blood or tissue concentrations of ethanol decline in an individual who had maintained prolonged heavy use of ethanol. After developing withdrawal symptoms, an individual is likely to consume ethanol to relieve or avoid those symptoms.

As used herein, the term "patient" means mammal; "mammal" means the Mammalia class of higher vertebrates; and the term "mammal" includes, but is not limited to, a human.

Ethanol use disorder includes ethanol abuse and ethanol dependence; the term dependence denotes a psychological and/or physiological manifestation of the dependence to ethanol. In particular, the term "ethanol use disorders" includes withdrawal disorders such as ethanol withdrawal with or without perceptual disturbances and ethanol withdrawal delirium. See DSM-IV-TR., Diagnostic and Statistical Manual of Mental Disorders. Revised, $4^{th}$ Ed., Text Revision (2000). Also, the International Classification of Diseases, Tenth Revision, (ICD-10) and updates provides classification for many of the disorders described herein. The skilled artisan will recognize that there are alternative nomenclatures and classification systems for the disorders described herein and those described in the DMS-IV-TR and ICD-10, and that terminology and classification systems evolve with medical scientific progress.

As used herein, the term "therapeutically effective amount" is synonymous with "therapeutically effective dose" and means an amount of the compound or a pharmaceutically acceptable salt that is sufficient in one or more administrations for treating ethanol use disorders, an anxiety disorder as described above, a depressive illness as described above, a combination of ethanol use disorder and one or both of an anxiety disorder and a depressive illness, schizophrenia, or a combination of ethanol use disorder and schizophrenia.

The term "treatment" and "treating" as used herein means the management and care of a patient for the purpose of diminishing or discontinuing self-administration and use of ethanol. The term is intended to include the full spectrum of intervention for the ethanol use disorder from which the patient is suffering, such as administration of the active compound to alleviate the symptoms or complications, to delay progression of the ethanol use disorder and to reduce the quantity of ethanol consumed per drinking day on a one month basis or heavy use days on a per month basis, or both. The management and care of a patient for the purpose of combating ethanol use disorder includes the administration of the active compound to inhibit the physiological or psychological onset of symptoms for resumption of use, continued use or enhanced use. The patient to be treated is preferably a mammal, in particular a human being. The term "treatment"

and "treating" as used herein also means the management and care of a patient for an anxiety disorder selected from panic disorder, obsessive-compulsive disorder, social phobia, generalized anxiety disorder, specific phobia and post-traumatic stress disorder; a depressive illness selected from major depression, dysthymia and bipolar disorder; or both; schizophrenia, and may further include ethanol use disorder in said patient.

The term is intended to include the full spectrum of intervention for the disorders from which the patient is suffering, such as administration of the active compound to alleviate the symptoms or complications, and to delay progression of the disorder. The patient to be treated is preferably a mammal, in particular a human being.

The spectrum of ethanol use ranges from none (abstinence) to low-risk use; then unhealthy use (excessive) which encompasses risky use and problem use; to ethanol use disorders which include ethanol abuse and ethanol dependence. Ethanol consumption is excessive when it causes or elevates the risk for ethanol related problems or complicates the management of other health problems. It should be appreciated that increasingly heavier drinking (heavy drinking days per month, amount consumed per drinking day over a month, or both) correlates with increasing adverse consequences to the patient and higher thresholds along the spectrum of ethanol use until the pattern reaches definitive stages of ethanol disease states (ethanol abuse and ethanol dependence). In the United States, men who drink five or more standard drinks in a day (or fifteen or more per week) and women who drink four or more in a day (or eight or more per week) are at risk for ethanol-related problems (i.e. risky use). In Europe, men who drink 4 units (32 g) per day and women who drink 3 units (24 g) per day are at risk for ethanol related problems (risky use). Individual responses to ethanol vary, however, and ethanol consumption at a risky use level may be a problem requiring treatment depending on many factors, such as age, co-existing conditions, and medication use.

A standard drink in the United States is any drink that contains about fourteen grams of pure ethanol (about 0.6 fluid ounces or 1.2 tablespoons). Standard drink equivalents are: 12 oz. of beer or cooler; 8-9 oz. of malt liquor; 5 oz. of table wine; 3-4 oz. of fortified wine (such as sherry or port); 2-3 oz. of cordial, liqueur or aperitif; 1.5 oz of brandy (a single jigger); and 1.5 oz. of spirits (a single jigger of 80-proof gin, vodka, whiskey, etc.). These are approximate, as different brands and types of beverages vary in their actual ethanol content. In Europe, one unit is a standard drink and comprises one-half pint of ordinary strength beer; a single measure of spirits; and a standard glass of wine. As with the United States measures, these are approximate as different brands and types of beverages vary in their actual ethanol content.

Pharmaceutically acceptable salts of the compound of the present invention and common methodology for preparing them are well known in the art. See, e.g., P. Stahl, et al., *Handbook of Pharmaceutical Salts: Properties Selection and Use*, (VCHA/Wiley-VCH, 2002); S. M. Berge, et al., "Pharmaceutical Salts," *Journal of Pharmaceutical Sciences*, Vol. 66, No. 1, January 1977.

The term "formulation", as in pharmaceutical formulation, or "pharmaceutical composition" is intended to encompass a product comprising (S)-3-fluoro-4-[4-[2-(3,5-dimethylphenyl)pyrrolidin-1-yl-methyl]phenoxy]benzamide, or a pharmaceutically acceptable salt thereof, or in admixture with its enantiomer, or a pharmaceutically acceptable salt thereof, and the inert ingredient(s) that make up the carrier. Accordingly, the pharmaceutical formulations encompass any composition made by admixing (S)-3-fluoro-4-[4-[2-(3,5-dimethylphenyl)pyrrolidin-1-yl-methyl]phenoxy]benzamide, or a pharmaceutically acceptable salt thereof, alone or in admixture with its enantiomer, or a pharmaceutically acceptable salt thereof, and a pharmaceutical carrier, diluent and/or excipient.

Compositions of the present invention comprising a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, and a therapeutically effective amount of a tertiary amine tricyclic norepinephrine reuptake inhibitor selected from amitriptyline, clomipramine, doxepin, imipramine and (+)-trimipramine, or a pharmaceutically acceptable salt thereof can conveniently be administered in a pharmaceutical composition containing the active components in combination with a suitable (pharmaceutically acceptable) carrier, diluent and/or excipient. Such pharmaceutical compositions can be prepared by methods and contain a carrier, diluent and/or excipients which are well known in the art. A generally recognized compendium of such methods and ingredients is Remington: The Science and Practice of Pharmacy Mack Publishing Co., 19$^{th}$ Ed., 1995). The compositions can be administered parenterally (for example, by intravenous) or orally. The amount of active compound in such therapeutically useful compositions is such that an effective dosage level will be afforded for each active ingredient.

It will be understood the compound of the present invention exists as a stereoisomer. As used herein, references to the compound of the present invention are meant to also include racemic mixtures thereof Herein, the Cahn-Ingold-Prelog designations of (R)— and (S)— are used to refer to specific isomers. Specific stereoisomers can be prepared by stereospecific synthesis using enantiomerically pure or enriched starting materials. The specific stereoisomers of either starting materials or compounds can be resolved by techniques well known in the art, such as those found in *Stereochemistry of Organic Compounds*, E. I. Eliel and S. H. Wilen (Wiley 1994) and *Enantiomers, Racemates, and Resolutions*, J., Jacques, A. Collet, and S. H. Wilen (Wiley 1991), including chromatography on chiral stationary phases, enzymatic resolutions, or fractional crystallization or chromatography of diastereomers formed for that purpose, such as diastereomeric salts. Where a chiral compound is resolved into its isomers, but absolute configurations or optical rotations are not determined, the isomers are arbitrarily designated as isomer 1, isomer 2, etc. While all mixtures containing the compound of the present invention are contemplated within the present invention, the preferred embodiment is a single enantiomer.

The compounds employed as initial starting materials in the synthesis of the compound of the present invention are well known and, to the extent not commercially available, are readily synthesized using specific references provided, by standard procedures commonly employed by those of ordinary skill in the art or are found in general reference texts.

Examples of known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001;

Advanced Organic Chemistry, 4th Edition, Part B, Reactions and Synthesis, Francis A. Carey and Richard J. Sundberg, Kluwer Academic/Plenum Publishers, 2000, etc., and references cited therein.

The tertiary amine tricyclic norepinephrine reuptake inhibitors amitriptyline, clomipramine, doxepin and imipramine are commercially available as hydrochloride salts. The compound (+)-trimipramine is commercially available as a maleate salt. The preparation of alternative pharmaceutically acceptable salts from the commercially available salt form is by standard procedures commonly employed by those of ordinary skill in the art.

As used herein, "equiv" refers to equivalents; "mg" refers to milligrams; "g" refers to grams; "kg" refers to kilogram; "mmol" refers to millimoles; "mL" refers to milliliters; "μm" refers to micrometer; "cm" refers to centimeter; "L" refers to liters; "° C." refers to degrees Celsius; "M" refers to molar; "Å" refers to Angstroms, "h" refers to hour or hours; "v/v" refers to the term "by volume" to describe the concentration of a substance in a mixture or solution; "DMA" refers to dimethylacetamide; "DCE" refers to dichloroethane; "AcOH" refers to acetic acid; "DCM" refers to dichloromethane; "EtOH" refers to ethanol; "MS" refers to mass spectrum; "APCI" refers to atmospheric pressure chemical ionization; "API" refers to atmospheric pressure ionization; "EIC" refers to extracted ion chromatography; "$t_R$" refers to retention time; the term "enantiomeric excess" or "ee" refers to the percent by which one enantiomer, E1, is in excess in a mixture of the two enantiomers, E1 plus E2, such that {(E1−E2)/(E+E2)}×100=% ee; "DTT" refers to dithiothreitol or Cleland's reagent; "HEPES" refers to N-(2-Hydroxyethyl)piperazine-N'-(2-ethanesulfonic acid); "EDTA" refers to ethylene diamine tetraacetic acid; "GTP" refers to guanosine 5'-triphosphate; "GDP" refers to guanosine 5'-diphosphate; "MTEP" refers to 3-[(2-methyl-1,3-thiazol-4-yl)ethynyl]pyridine; "sc" refers to subcutaneous; "ip" refers to intraperitoneal; "po" refers to per os (oral); "i.v." refers to intravenously.

Preparation of Intermediate 1

3-Fluoro-4-(4-formyl-phenoxy)-benzonitrile

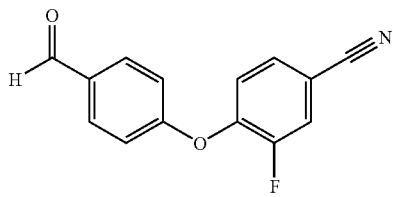

Stir a mixture of 4-hydroxy-benzaldehyde (50 g, 1.00 equiv, 409.4 mmol) and 3,4-difluoro-benzonitrile (56.96 g, 1.00 equiv) in DMA (750 mL) at 23° C. until completely dissolved. Add potassium carbonate (1.5 equiv, 84.88 g) and heat the mixture at 100° C. for 3 h. Cool to room temperature. Pour the reaction mixture over $H_2O$-ice (1.5 L). Filter the solid over filter paper, wash the solid with water twice, and dry under reduced pressure to obtain Intermediate 1. (82.40 g, 83% yield). MS (APCI): ($M^+$1) 240.0

Preparation of Intermediate 2

3-Fluoro-4-(4-formyl-phenoxy)-benzamide

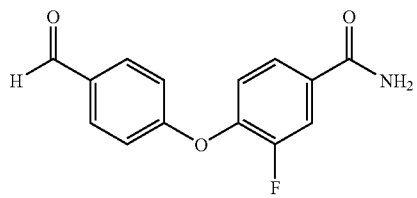

To a stirred solution of 3-fluoro-4-(4-formyl-phenoxy)-benzonitrile (17.72 g, 1.00 equiv; 73.460 mmol) in dimethyl sulfoxide (75 mL), add potassium carbonate (0.5 equiv, 5.08 g). Cool the mixture to 10° C. and add hydrogen peroxide (35% in water, 7.4 mL, 1.05 equiv) dropwise, keeping the internal temperature below 40° C. After the addition, stir the reaction mixture for 3 h. Pour the mixture over $H_2O$-ice (300 mL). Filter the solid over filter paper, wash the solid with water twice, and dry under reduced pressure to obtain Intermediate 2. (17.30 g, 91% yield). MS (APCI): ($M^+$+1)260.1

EXAMPLE 1

4-{4-[2-(3,5-Dimethyl-phenyl)-pyrrolidin-1-ylmethyl]-phenoxy}-3-fluoro-benzamide

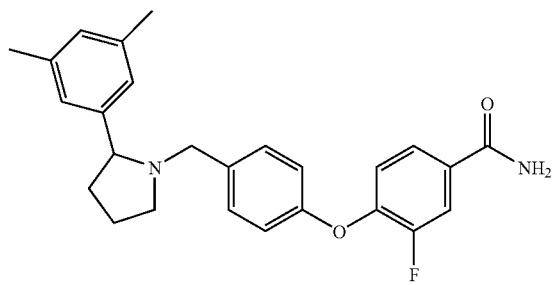

Part 1—Racemic 4-{4-[2-(3,5-Dimethyl-phenyl)-pyrrolidin-1-ylmethyl]-phenoxy}-3-fluoro-benzamide Add a solution of 3-fluoro-4-(4-formyl-phenoxy)-benzamide in DCE:AcOH, 25:2 (100 mg, 1 eq in 6.7 mL, 0.06 M) to 2-(3, 5-Dimethyl-phenyl)-pyrrolidine (70 mg, 0.4 mmol, 1 eq) in a sealed tube. Orbitally stir the mixture for 16 h at room temperature. Add sodium triacetoxyborohydride (1.5 eq; 127 mg) in two portions. Stir the mixture at room temperature for 10 h. Remove the solvent under a stream of $N_2$ gas at 40° C. overnight. Dissolve the crude reaction mixture in DCM and adsorb onto Stratta-$NH_2$® (55 microns, 70 Å) Phenomenex, Inc., 411 Madrid Avenue, Torrance, Calif., 90501-1430, U.S.A. Purify by flash chromatography on $SiO_2$ cartridge using a gradient of $CHCl_3$: EtOH:$NH_4OH$ (97:3:0.3 to 88:12:

1.2) to afford the title compound (100 mg, 60%) as a racemic mixture. MS (EIC): (M+1) 419

Part 2

4-{4-[2-(3,5-Dimethyl-phenyl)-pyrrolidin-1-ylmethyl]-phenoxy}-3-fluoro-benzamide Isomers 1 and 2

Isomer 1

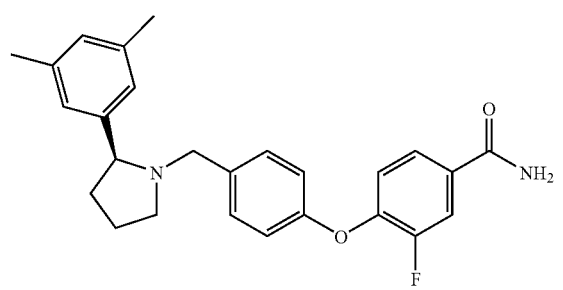

Example 1A

Isomer 2

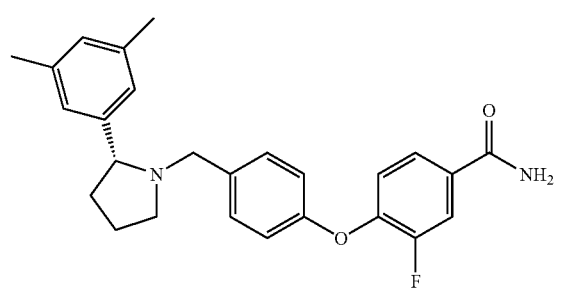

Example 1B

A racemic mixture (40 mg) of enantiomers from Example 1, Part 1, is purified by chiral chromatography using Chiralpak AD (250 mm×4.6 mm, 10 μm) eluting with Hex-0.2% DMEA/EtOH 90/10; Flow rate 1 ml/min; $t_R$=6.7 min, to afford the isomer 1 compound (9.6 mg). Purity (%) by LC/MS: 99%, ee (%) 98%; MS (EIC): (M+1) 419 (referred to herein as Example 1A). A second eluting enantiomer (9.7 mg), $t_R$=12.9 min. is designated as the isomer 2 compound (referred to herein as Example 1B). Purity (%) by LC/MS: 99%, ee (%) 98%; MS (EIC): (M+1) 419.

The absolute configuration of Isomer 1 (Example 1A) and Isomer 2 (Example 1B) are determined to be, respectively, (S) and (R), using the well known Mosher method. Generally, this method involves derivatization of a chiral substrate with the two enantiomers of the chiral reagent alpha-methoxy-alpha(trifluoromethyl)phenyl acetic acid (MTPA), followed by the comparative analysis of the $^1$H NMR spectra of the resulting diastereomers. It is also possible to determine absolute configuration of 2-phenylpyrrolidines by the multiplicity of the H2 signal. If the configuration of the MTPA moiety in the Mosher's amide is (R) and the H2 signal is a doublet of doublets (one of the couplings is roughly twice the other) the absolute configuration of the amine under examination is (S). If this signal is an apparent triplet (both couplings are similar) the absolute configuration is (R). Conversely, if the configuration of the MTPA auxiliary is (S), H2 appears as a triplet in the (S)-2-phenylpyrrolidine and as a doublet of doublets in the (R)-2-phenylpyrrolidine. Further, details are available in P. Vidal, et al., *Organic Letters*, 9 (21), 4123-4126 (2007).

As described above, a racemic mixture of enantiomers is prepared and separated into Examples 1A and 1B by chiral chromatography. A preferred method of preparing Example 1A is enantioselective synthesis using enantiomerically pure 2-(3,5-dimethylphenyl)pyrrolidine and substantially following the procedures described above in Example 1, Part 1.

As noted above, the compound of Example 1A, or a pharmaceutically acceptable salt thereof, is a selective antagonist, or in selectively blocking the effect of agonists, at the kappa opioid receptor. Features of the compound of Example 1A are one or more of its structural features and biological properties afforded by those features including kappa receptor selectivity (binding affinity), kappa receptor activity (antagonist potency), efficacy at reducing ethanol intake in small animal models, bioavailability in small animal models and tolerability regarding undesirable side effects in small animal models. In addition, the compound of Example 1A evidences anxiolytic, antidepressant and antipsychotic activity in small animal model assays.

As used herein, kappa opioid receptor selectivity means in vitro binding affinity at the kappa receptor of less than 1 nM and more particularly less than or equal to 0.6 nM.

In contrast, in vitro binding affinity at the mu and delta opioid receptors are greater than 5 nM and generally greater than 8 nM.

Also, as used herein, selective kappa opioid receptor antagonist potency means in vitro competitive binding displacement of a known agonist at less than 6 nM and more particularly less than 3 nM.

In contrast, in vitro competitive binding displacement of known mu and delta receptor agonists is greater than 15 nM and generally greater than 20 nM.

The compound of the present invention is described as a selective kappa opioid receptor antagonist. This description is intended to include both "neutral antagonist" and "inverse agonist" within its scope. A "neutral antagonist" is a reversible receptor ligand without intrinsic activity. It does not influence the receptor's own basal activity (constitutive receptor activity) and prevents binding, in a competitive manner, of an agonist (endogenous or non-endogenous) to the receptor. An "inverse agonist" is a ligand with negative intrinsic activity. It inhibits the receptor's own activity (constitutive receptor activity) by shifting the equilibrium of the receptor conformation to its inactive state and inhibits binding of an agonist to the receptor. In a high constitutive receptor activity environment, an inverse agonist will differentiate itself from a neutral antagonist.

The compound of Example 1A or a pharmaceutically acceptable salt thereof is effective over a wide dosage range in the treatment of ethanol use disorders and in treating independent comorbid anxiety and/or depression or schizophrenia that may also be present. For example, dosages per day will normally fall within the range of about 0.05 to about 50 mg/kg of body weight. In the treatment of adult humans, the range of about 0.5 to about 50 mg/kg, in single or divided doses, is typical. However, it will be understood that the amount of the compound actually administered will be determined by a physician in light of the relevant circumstances, including the condition or comorbid conditions to be treated, the age, weight, and response of the individual patient, the severity of the patient's symptoms, and the chosen route of administration, and therefore the above dosage ranges are not intended to limit the scope. It should also be understood that the amount of compound administered should be within a dose range that affords selective central kappa receptor occupancy and does not appreciably block mu or delta opioid, or other, receptors. The compound may be administered by a variety of routes such as oral, transdermal, subcutaneous, sublingual, intranasal, intramuscular or intravenous routes.

As is well known, the dosage of each component in a two component medicament depends on several factors such as the potency of the selected specific compound, the mode of administration, the age and weight of the patient, the severity of the condition to be treated, and the like. This is considered to be within the skill of the artisan and one can review the existing literature to determine optimal dosing for the tertiary amine tricyclic norepinephrine reuptake inhibitor component.

The average daily adult dosage of the norepinephrine reuptake inhibitors are:

|  | Broad Dose mg/day | Usual Dose mg/day |
| --- | --- | --- |
| amitriptyline | 25-300 | 100-200 |
| clomipramine | 25-250 | 100-200 |
| doxepin | 25-300 | 100-200 |
| imipramine | 25-300 | 100-200 |
| (+)-trimipramine | 25-300 | 75-200 |

Those compositions, containing two active components, may be administered in the same physical form or concomitantly according to the above described dosages. The dosages for each active component can be measured separately and can be given as a single combined dose or given separately. They may be given at the same or at different times as long as both actives are in the patient at one time over a 24-hour period. Concomitant or concurrent administration means the patient takes one drug within about 5 minutes of taking the other drug. Because the goal is to provide rapid symptomatic relief to the patient, in most cases when treatment is started the two drugs would be administered to the patient close in time and typically concomitantly; thereafter, the timing of each drug's administration may be adjusted so long as both agents are active in the patient at the same time over a 24-hour period.

The criteria for ethanol dependence set forth in DSM-IV-TR is a pattern of ethanol use, leading to clinically significant impairment or distress as manifested by at least three selected from the following group, occurring at any time within the same twelve month period: (1) tolerance as defined by either (a) a need for substantially increased amounts of ethanol to achieve intoxication or the desired effect; or (b) substantially diminished effect with continued use of the same amount of ethanol; (2) withdrawal, as demonstrated by either (a) the characteristic withdrawal syndrome for ethanol; or (b) the same, or a closely related substance is taken to relieve or avoid withdrawal symptoms; (3) ethanol is often taken in larger amounts or over a longer period then was intended; (4) there is a persistent desire or unsuccessful efforts to cut down or control ethanol use; (5) a great deal of time is spent in activities necessary to obtain ethanol, use ethanol, or recover from its effects; (6) important social, occupational or recreational activities are given up or reduced because of ethanol use; and (7) ethanol use is continued despite knowledge of having a persistent or recurrent physical or psychological problem that is likely to have been caused or exacerbated by ethanol.

Ethanol dependence can be with physiological dependence; that is evidence of tolerance or withdrawal is present, or without physiological dependence, where no evidence of tolerance or withdrawal is present. However, it should be understood that so-called "psychological dependence" may be the result of a protracted withdrawal where physical symptoms are not readily detected and often manisfested as psychological complaints such as dysphoria or anhedonia.

The essential feature of ethanol abuse is a maladaptive pattern of ethanol use manifested by recurrent and significant adverse consequences related to the repeated use of ethanol. In order for an abuse criterion to be met, the ethanol-related problem must have occurred repeatedly during the same 12-month period or been persistent. There may be repeated failure to fulfill major role obligations, repeated use in situations in which it is physically hazardous, multiple legal problems, and recurrent social and interpersonal problems. Unlike the criteria for ethanol dependence, the criteria for ethanol abuse do not include tolerance, withdrawal, or a pattern of compulsive use and instead include only the harmful consequences of repeated use. A diagnosis of ethanol abuse is preempted by the diagnosis of ethanol dependence if the individual's pattern of ethanol use has ever met the criteria for dependence.

Further information and details regard ethanol use disorder that is treated by the present compound, or a pharmaceutically acceptable salt thereof, is found in DSM-IV-TR.

The independent comorbid anxiety disorders treated by the present compound, or a pharmaceutically acceptable salt thereof, are selected from panic disorder, obsessive-compulsive disorder, social phobia, generalized anxiety disorder, specific phobia, and posttraumatic stress disorder. These disorders may be treated alone or concomitantly with ethanol use disorder in a patient. The particular anxiety disorders contemplated as treatable comorbid conditions are as defined in DSM IV TR, and described in United States Department of Health and Human Services, National Institute of Mental Health, NIH Publication No. 06-3879.

Further information and details regarding the anxiety disorders described above and treated by the present compound, or a pharmaceutically acceptable salt thereof, are found in DSM-IV-TR.

The independent comorbid depression illnesses treated by the present compound, or a pharmaceutically acceptable salt thereof, are selected from major depression, dysthymia and bipolar disorder. These disorders may be treated alone or concomitantly with ethanol use disorder in a patient. The particular depressive illnesses contemplated as treatable comorbid conditions by the present invention are as defined in DSM IV TR and described in United States Department of Health and Human Services, National Institute of Mental Health, NIH Publication No. 02-3561.

Further information and details regarding the depression disorders described above and treated by the present compound, or a pharmaceutically acceptable salt thereof, are found in DSM-IV-TR.

The independent comorbid schizophrenia treated by the present compound, or a pharmaceutically acceptable sat thereof, includes the subtypes paranoid, disorganized, catatonic, undifferentiated and residual. This disorder may be treated alone or concomitantly with ethanol use disorder in a patient. The schizophrenia contemplated as a treatable comorbid condition by the present invention is as defined in DSM IV TR.

Further information and details regarding schizophrenia treated by the present compound, or a pharmaceutically acceptable salt thereof, are found in DSM-IV-TR.

As previously noted, an anxiety disorder, as described above, a depression illness, as described above, and ethanol use disorder may be simultaneously treated by the compound of the present invention, or a pharmaceutically acceptable salt thereof; or schizophrenia as described above, and ethanol use disorder may be simultaneously treated by the compound of the present invention, or a pharmaceutically acceptable salt thereof.

The compound of Example 1A is preferably administered in connection with and/or subsequent to an educational and/or behavioral modification program to enhance diminution in frequency and/or quantity of use or abstinence from ethanol. The programs may be more effective by focusing on educational and behavioral modification goals, reducing the incidence of program non-completion.

As noted above, the compound of Example 1A is a kappa opioid receptor selective antagonist. The selectivity is demonstrated in both in vitro and in vivo assays. All ex vivo and in vivo experiments are performed according to the policies of the Animal Care and Use Committee of Eli Lilly and Company, in compliance with the American Association for the Accreditation of Laboratory Animal Care-approved guidelines.

Kappa Affinity In Vitro

GTP-γ-S Binding Assay

A scintillation proximity assay (SPA)-based GTP-γ-$S^{35}$ assay format is carried out substantially in accordance with (Emmerson et al., *J. Pharm Exp Ther.* 278,1121 (1996); Horng et al., *Society for Neuroscience Abstracts*, 434.6 (2000) and (DeLapp et al., *JPET* 289, 946 (1999) assay formats. Membranes are re-suspended in 20 mM HEPES, 100 mM NaCl, 5 mM $MgCl_2$, 1 mM DTT, and 1 mM EDTA. Fifty μL of GTP-γ-[$^{35}$S], compound, membrane suspension (20 microgram/well), and wheat germ agglutinin coated SPA beads (WGA PVT SPA, GE Healthcare, 800 Centennial Avenue, Piscataway, N.J. 08854) (1 mg/well) are added to clear bottom 96 well assay plates. GDP (200 μM to achieve a 50 μM final concentration per well) is added to the membrane solution prior to addition to the assay plates. Plates are sealed and incubated for four hours at room temperature then placed in a refrigerator overnight to allow the beads to settle. Signal stability at 4° C. is determined to be >60 hours. Plates are warmed to room temperature and counted in a Wallac Micro-Beta® scintillation counter (Perkin Elmer Life and Analytical Sciences, 549 Albany Street, Boston, Mass. 02118 USA. For antagonist assays, specific agonists are added at the following concentrations: mu-opioid receptor (MOR) DAMGO ([D-$Ala^2$, N-Me-$Phe^4$, $Gly^5$-ol]-Enkephalin, Sigma-Aldrich catalog number E7384) 1 micromolar; delta-opioid receptor (DOR) DPDPE ((D-$Pen^2$, D-$Pen^5$)-Enkephalin, Bachem Catalog number H-2905) 30 nM; and kappa-opioid receptor (KOR) U69593 ((+)-(5α,7α,8β)-N-Methyl-N-[7-(1-pyrrolidinyl)-1-oxaspiro[4.5]dec-8-yl]-benzeneacetamide, Sigma-Aldrich Catalog number U103) 300 nM. Kb values are determined using a modification of the Cheng-Prusoff equation (see Cheng and Prusoff, *Biochem. Pharmacol.* 22, 3099 (1973) as previously reported (DeLapp et al., 1999). For n>1 evaluations, the summarized averaged values are a geometric mean of the stated number of runs (n=2 or 3) calculated as Mean Log Kb=Average (Kb1+Kb2+Kb3); SE=STDEV (Kb1+Kb2+Kb3)/SQRT n (n=2 or 3); Geometric mean Kb (nM)=10^Mean Log Kb; SEM=SE×Geometric mean Kb (nM)×LN(10).

TABLE 1

| | Opioid Receptor In Vitro Antagonism GTP-γ-S Kb (nM) | | |
|---|---|---|---|
| Example No. | hMu | hKappa | hDelta |
| 1 (racemic) | 56.7 (n = 1) | 5.43 (n = 1) | 293 (n = 1) |
| 1A (isomer 1) | 40.1 (21.3, n = 3) | 2.12 (1.06, n = 3) | 264 (111, n = 3) |
| 1B (isomer 2) | 69.6 (22.8, n = 2) | 44.8 (14.7, n = 2) | 220 (149, n = 2) |

The Ki values are determined using the Cheng and Prusoff, (supra) equation Ki=EC50/(1+[ligand]/Kdx) and are reported below in Table 2. For n>1 evaluations, the summarized averaged values are a geometric mean of the stated number of runs (n=2 or 3) calculated as Mean Log Ki=Average (Ki1+Ki2+Ki3); SE=STDEV (Ki1+Ki2+Ki3)/SQRT n (n=2 or 3); Geometric mean Ki (nM)=10^Mean Log Ki; SEM=SE×Geometric mean Ki (nM)×LN(10). These data show the compound of Example 1 (racemic) and particularly the compound of Example 1A (isomer 1) are potent opioid receptor antagonists selective for the kappa receptor relative to the mu and delta receptors.

TABLE 2

| | In Vitro Binding High $Na^+$/GDP Ki (nM) | | |
|---|---|---|---|
| Example No. | Mu | Kappa | Delta |
| 1 (racemic) | 12 (n = 1) | 0.225 (n = 1) | 170 (n = 1) |
| 1A (isomer 1) | 16.4 (8.25, n = 3) | 0.597 (0.373, n = 3) | 122 (38.6, n = 3) |
| 1B (isomer 2) | 101 (33.7, n = 2) | 13.9 (0.293, n = 2) | 165 (18.6, n = 2) |

These data show the compound of Example 1 (racemic) and particularly the compound of Example 1A (isomer 1) selectively bind the kappa opioid receptor relative to the mu and delta receptors.

Opioid Receptor Occupancy (RO) in Rat Brain

In order to bridge in vitro potency to in vivo efficacy and to evaluate the occupancy of the compound of the present invention at opioid receptors, an in vivo rat model for monitoring opioid RO is employed. In this assay, microdoses of naltrexone (10 μg/kg) ((5α)-17-(Cyclopropylmethyl)-4,5-epoxy-3,14-dihydromorphinan-6-one), naltriben (10 μg/kg) (17-(Cyclopropylmethyl)-6,7-didehydro-3,14b-dihydroxy-4,5α-epoxy-5,7-2',3'-benzo[b]furanomorphinan) and GR 103545 ([(-)-(R)-Methyl 4-[(3,4-dichlorophenyl)acetyl]-3-1[(1-pyrrolidinyl)methyl]-1-piperazinecarboxylate) (1.5 μg/kg) are simultaneously administered intravenously in a single injection and used as RO tracers for mu, delta and kappa receptors, respectively. Administration of the three tracers permits one to understand the relative selectivity of the opioid receptor subtypes occupied and the degree of receptor occupancy that occurs at any specific subtype at efficacy. In RO, the distribution of the tracer in various brain regions is measured by LC/MS/MS (API 4000, MDS Sciex) providing a nonradioactive method for detecting the amounts of tracer in brain with high sensitivity. Receptor occupancy is then calculated as the difference in specific accumulation of tracer in animals treated with a compound of the present invention versus animals treated with vehicle alone. In this method the striatum (a region of high mu, delta and kappa opioid receptor density) is taken for specific tracer accumulation while the cerebellum (a brain region devoid of opioid receptors) represents nonspecific tracer accumulation. Receptor occupancy is determined 90 minutes following a single oral dose of a compound of the present invention or 5.5 hrs following administration for dose-response evaluation. Data represent the mean±SEM of receptor occupancy in 3-6 rats per dose group with each rat weighing approximately 230 g.

Male Harlan Sprague Dawley rats are treated with the compound of Example 1A of the present invention using a 3% lactic acid/water oral formulation at doses of 0.03, 0.01, 0.3, 1, 3, 10 and 30 mg/kg. The test animals exhibited a dose-dependent level of kappa receptor occupancy in the striatum 5.5 hrs following oral administration. The calculated ED50 for kappa receptor occupancy of the compound of Example 1A of the present invention was 0.45 mg/kg. Consistent with the in vitro binding data, the compound of Example 1A of the present invention displayed high selectivity for the kappa opioid receptor in vivo, producing no significant occupancy of either mu or delta (measured in the striatum) receptors at doses up to 30 mg/kg meaning the ED50 at those receptors is greater than 30 mg/kg. The increasing levels of kappa receptor occupancy are driven by roughly proportional increases in plasma and brain exposure of the compound of Example 1A of the present invention up to a dose of 30 mg/kg. These data support that following oral administration the compound of Example 1A selectively binds to kappa opioid receptors in the rat brain with high potency.

Exposure levels of the compound of Example 1A in the rat striatum following administration were determined in the same samples used to quantify the level of opioid receptor occupancy. Levels of Example 1A are detected by LC/MS/MS (API 4000, MDS Sciex) and quantified from a standard curve of Example 1A prepared in rat brain homogenate.

TABLE 3

Brain Levels

| Example 1A oral dose mg/kg | Example 1A ng/g tissue | SEM | n |
|---|---|---|---|
| 30 | 265.67 | 46.25 | 3 |
| 10 | 171.47 | 78.53 | 3 |
| 3 | 39.20 | 8.67 | 3 |
| 1 | 19.63 | 11.05 | 3 |
| .3 | 7.23 | 0.42 | 3 |
| .1 | 15.30 | 7.29 | 3 |

Plasma exposure of Example 1A of the present invention in the rat following administration is determined from plasma isolated from trunk blood collected at the time of tissue collection for receptor occupancy. Levels of the compound of Example 1A are detected by LC/MS/MS (API 4000, MDS Sciex) and quantified from a standard curve of Example 1A prepared in vehicle treated rat plasma.

TABLE 4

Plasma Levels

| Example 1A oral dose | Example 1A ng/g | SEM | n |
|---|---|---|---|
| 30 | 106.03 | 22.22 | 3 |
| 10 | 65.20 | 29.08 | 3 |
| 3 | 15.43 | 3.54 | 3 |

TABLE 4-continued

Plasma Levels

| Example 1A oral dose | Example 1A ng/g | SEM | n |
|---|---|---|---|
| 1 | 4.63 | 1.63 | 3 |
| .3 | 2.27 | 0.79 | 3 |
| .1 | 1.17 | 0.47 | 3 |

P-Rat Protocol

P Rat 12 hr Ethanol Drinking

The test animals are selectively-bred alcohol preferring (P) rats. These rats voluntarily consume more than 5 g/kg of ethanol per day and meet all of the perceived criteria for an animal model of alcoholism. They attain blood alcohol contents between 50-200 mg %; they will operant respond to obtain ethanol; they consume ethanol for pharmacological effects and not taste, smell or caloric properties; and they develop metabolic and physiological tolerance and eventually dependence with chronic ethanol access.

Animals

Female P rats are obtained from a breeding facility at the Indiana University Medical Center in Indianapolis, Ind., USA. Rats are individually housed in an environmentally controlled facility and maintained on a 12 hr light/dark cycle (lights off at 1500 hours).

Compounds

All drugs are mixed fresh prior to use and administered in a volume of 1 mL/kg. Compounds are solubilized in sterile water by the dropwise addition of 85% lactic acid. Unless otherwise stated, compounds are administered p.o. prior to the onset of the dark cycle using a counterbalanced, within-subject design (n=8-11 per experiment).

Experimental Procedure

Following a 4-day acclimation to the colony, rats receive homecage access to a bottle of EtOH (10% v/v; Ancare, Bellmore, N.Y.) in addition to the standard bottle of water. Access to water and 10% EtOH, as well as standard laboratory chow, are freely available. Once rats reach a stable level of daily intake, the EtOH solution is increased to 15% v/v. Consumption of EtOH and water are monitored for approximately 6-9 months prior to drug testing. Food and fluid intake are measured via force transduction with a PC-controlled Drinking & Feeding Monitoring System (TSE Systems, Bad Homburg, Germany). Consumption of food, water, and 15% (v/v) EtOH are continuously monitored for 12 hrs following drug or vehicle administration. For some experiments, continuous monitoring for 24 hours is carried out.

At 1 mg/kg and 3 mg/kg administered orally, the compound of Example 1A decreased the amount of ethanol consumed (p<0.05 versus vehicle).

P Rat Progressive Ratio Responding for Ethanol

This test assesses the motivation to work for access to ethanol in P rats following ethanol abstinence. This animal model simulates ethanol craving.

Female P rats (Indiana University Medical Center, Indianapolis, Ind., USA) are pair-housed in an environmentally controlled facility and maintained on a 12 h light/dark cycle (lights on at 0600 hours).

Compounds are solubilized in sterile water by the dropwise addition of 85% lactic acid, mixed freshly prior to use, and administered in a volume of 1 mL/kg. Unless otherwise stated, compounds are administered p.o. 60 min prior to the experimental session. Doses are assigned using a counterbalanced, within-subject design (n=8-11 per experiment).

In order to reduce novelty-induced avoidance of ethanol (EtOH), the water bottle on the homecage is replaced with a bottle containing 15% EtOH (v/v; Ancare, Bellmore, N.Y.) for two days prior to operant training. Throughout the rest of the experiment, rats are allowed ad libitum access to water and standard laboratory chow in the homecage.

Daily 60-min sessions are conducted in standard rat operant chambers, housed within sound-attenuating chambers (MED Associates, Inc., St. Albans, Vt., USA). The 0.5 cm diameter stainless steel bars of the floor grid of the operant chambers are positioned approximately 1.5 cm apart. Two retractable operant levers in each operant chamber are located approximately 15 cm above the grid floor and 13 cm apart. A recessed trough is located in the space between the levers, through which a dipper cup (0.1 mL capacity) is raised to deliver response-contingent ethanol (15% EtOH, v/v). Upon a reinforced response, a stimulus light is illuminated during the 4-sec dipper cup access. Operation of the stimuli and behavioral responses are controlled and recorded by personal computer for offline analysis. At the end of each session, all stimuli are turned off and levers are retracted.

Rats are trained to press a lever for EtOH reinforcement. Initially, responses on either lever are considered correct responses and are rewarded with reinforcement. Access to the reinforcement is signaled by illuminating a stimulus light above the lever on which the response is made. Once rats learn to press a lever to obtain EtOH reward, the response contingency is changed so that responses made on one lever (active lever) are reinforced, using a fixed-ratio (FR)-1 schedule of reinforcement, while responses on the other (inactive) lever are not reinforced. Over a period of 3-4 weeks, the response contingency is increased to FR-3, such that 3 lever presses are required for each reinforcement. Once a stable level of responding is reached, the response contingency is changed to a progressive ratio schedule of reinforcement. For this procedure, the response requirement is slowly increased throughout the experimental session such that rats work progressively harder to receive the EtOH reward. Specifically, the response requirement is increased as follows: all rats begin at an FR-1 schedule of reinforcement; after three reinforcements, the schedule is increased to FR-2; after three reinforcements at that level, the schedule is increased to FR-4; after three reinforcements at FR-4, the schedule is increased to FR-6; and so on. Each session is scheduled to last a total of 60 min. The amount of EtOH that is consumed (in mL and g/kg) is recorded, as well as the number of responses on the active and inactive levers, and the breakpoint, which is defined as the highest FR value reached during the session.

The compound of Example 1A is administered p.o. 60 min. prior to testing at 1, 3, and 10 mg/kg. The number of active lever responses is reduced following administration of 10 mg/kg ($p<0.05$ versus vehicle). The quantity of ethanol consumed and the breakpoint are also reduced at the 10 mg/kg dose ($p<0.05$ versus vehicle). The data evidences a reduction in motivation to work for access to ethanol despite their extensive operant history for ethanol.

Stress-Induced Hyperthermia (in Rat)

Hyperthermia is a general phenomenon that has been reliably demonstrated in many species in response to stress, and is a component of the well-characterized fight-or-flight response. This test evaluates a test compound as a measure of its anxiolytic effects. The conventional and minimally-invasive method for analyzing stress-induced hyperthermia is by measuring body temperature, and stress-induced increases in body temperature, via rectal thermometer. This procedure entails dosing the animals prior to measuring the baseline body temperature reading (baseline temperature, T1). The handling by the experimenter and insertion of the rectal probe produce a moderate increase in body temperature that peaks within 10-15 minutes. A second body temperature measurement (T2) is recorded 10 minutes after the first measurement. The change in body temperature (T2 minus T1) is defined as the stress-induced hyperthermic response.

Male Fischer F-344 rats (Harlan, Indianapolis, Ind., USA) weighing between 275-350 g are tested. All animals are individually-housed with food and automated water available ad libitum, and maintained on a 12 h light/dark cycle (lights on at 06:00). On the day prior to each experiment, food is removed from home cages of rats designated for test, so that the animals are fasted for approximately 12-18 hours before the experiment. Rats are transported from the colony room in groups of n=10, to a procedure room for dosing. Rats are dosed po in a dose volume of 1 mL/kg with test compounds in the range of 1, 3, and 10 mg/kg dissolved in sterile water with the dropwise addition of 85% lactic acid. A solution of the metabotropic glutamate subtype 5 (mGlu5) antagonist 3-[(2-methyl-1,3-thiazol-4-yl)thynyl]pyridine (MTEP) (10 mg/kg) dissolved in water is used as a positive control. Immediately following dosing, rats are returned to their home cage, and the experimenter turns off the lights and leaves the room. The dosing room (Room A) is darkened for the remainder of the 60 min pretreatment period.

After the pretreatment period, rats are taken individually to a brightly lit adjacent room (Room B) where baseline body temperatures are determined by insertion of the rectal probe lubricated with mineral oil. Body temperature is assessed using a Physitemp® BAT-12 Microprobe Thermometer with a Physitemp® RET-2® rat rectal probe (Physitemp Instruments Inc., 154 Huron Ave. Clifton, N.J. 07013). The probe is inserted approximately 2 cm into the rectum. The core body temperature is measured (this is the baseline body temperature, T1, in degrees C). The rat is then placed back in the homecage, and remains in Room B. Ten minutes later a second body temperature measurement is recorded (T2). The difference between the first and second body temperature measurements (T2−T1) is used as an index of stress-induced hyperthermia.

A second study evaluating a combination of the compound of Example 1A dosed together with a sub-threshold dose of chlordiazepoxide (CDP) is carried out.

For the drug combination study, Example 1A (1, 3, and 10 mg/kg, po, 60 min pretreatment) is dosed together with chlordiazepoxide 1 mg/kg, po, water vehicle), and 1 mg/kg chlordiazepoide alone is used as the positive control.

Study 1. The compound of Example 1A is administered p.o. 60 min. prior to measurement of baseline core body temperature at 1, 3, and 10 mg/kg. The compound produces a dose-dependent, but non-significant, reduction in stress-induced hyperthermia (T2−T1). Importantly, baseline core body temperature is not affected. The positive control compound significantly reduces stress-induced hyperthermia ($p<0.05$), without affecting baseline body temperatures.

Study 2. The compound of Example 1A is administered p.o. at 1, 3, and 10 mg/kg, together with 1 mg/kg chlordiazepoxide, 60 min. prior to measurement of baseline core body temperature. Separate groups receive either 10 mg/kg Example 1A alone or 1 mg/kg chlordiazepoxide alone (p.o., 60 min prior to baseline body temperature). The compound of Example 1A increases the efficacy of a sub-threshold dose of chlordiazepoxide to produce a significant reduction in stress-induced hyperthermia (p<0.05). Importantly, baseline core body temperature is not affected.

Study 1. Compound of Example 1A alone: Vehicle=0.98±0.10; 1 mg/kg Example 1A=0.84±0.07, 3 mg/kg Example 1A=0.80±0.10; 10 mg/kg Example 1A=0.75±0.11; MTEP control=0.42±0.09.

Study 2. Compound of Example 1A and chlordiazepoxide: Vehicle=0.86±0.06; 1 mg/kg CDP alone=0.75±0.06; 10 mg/kg Example 1A alone=0.74±0.04; 1 mg/kg Example 1A and CDP=0.68±0.06; 3 mg/kg Example 1A and CDP=0.70±0.07; 10 mg/kg Example 1A and CDP=0.57±0.07.

The data from Studies 1 and 2 evidence the compound of Example 1A, alone, has a modest anxiolytic effect. However, in combination with a benzodiazepine, a more robust anxiolytic effect is seen with the compound of Example 1A at lower doses. These data suggest the use of the compound of Example 1A alone, or as an adjunctive treatment with a benzodiazepine anxiolytic agent for anxiety disorders.

Mouse Forced Swim Test

This test evaluates the effect of test compound on mice mobility as a measure of antidepressant effect. The less immobility compared to vehicle, the more pronounced the antidepressant-like effect.

Male, NIH-Swiss mice (25-30 g) (Harlan Sprague-Dawley, Indianapolis, Ind., USA) are housed in a vivarium for at least one week prior to use with water and rodent chow freely available during this acclimation period. Animals are removed from the vivarium to the testing area in their home cages and allowed to adapt to the new environment for at least one hour before testing.

Mice are placed in clear plastic cylinders (diameter: 10 cm; height: 25 cm) filled with 6 cm of water (22-25° C.) for six minutes. The duration of immobility during the last four minutes of the six minutes test period is scored. A mouse is recorded as immobile when floating motionless or making only those movements necessary to keep its head above water.

The test compound is administered p.o. 1 hour prior to testing at 1.0 mg/kg, 3.0 mg/kg and 10.0 mg/kg, n of 8 per group in a vehicle of 5 ml of sterile water and 30 ml of diluted (10×) lactic acid. Imipramine is evaluated as a positive control, 15 mg/kg: p, 30 min. prior to testing n of 4. At 10.0 mg/kg, the compound of Example 1A demonstrates antidepressant-like activity (p<0.05 versus vehicle, Dunnett's test).

A second study is carried out evaluating 1 and 3 mg/kg doses of the compound of Example 1A alone and in combination with 5 mg/kg of imipramine. Imipramine alone is evaluated at 5 and 15 mg/kg doses and a vehicle control is included in the study. For the combination studies, the compound of Example 1A is administered p.o. 30 minutes prior to administration of imipramine i.p. and the test initiated 30 minutes following imipramine administration. An n of 8 per group is evaluated for all groups. For the evaluations of the compound of Example 1A alone, testing is initiated 60 minutes following administration and testing of imipramine only treated animals is initiated 30 minutes following administration. A 3 mg/kg dose of the compound of Example 1A and 5 mg/kg of imipramine was substantially as efficacious as a 15 mg/kg dose of imipramine alone and statistically significant over each of vehicle control, imipramine 5 mg/kg alone and 3 mg/kg of Example 1A alone. The 1 mg/kg dose of the compound of Example 1A and 5 mg/kg imipramine also evidenced statistically significant antidepressant effects over each of vehicle control, imipramine 5 mg/kg alone and 1 mg/kg of Example 1A alone. As in the initial study, imipramine 15 mg/kg demonstrated statistically significant antidepressant effect over vehicle control (p<0.05, Dunnett's test for all statistical evaluations).

TABLE 5

Effect of Example 1A and Imipramine on immobility in mouse forced swim test

| Treatment | Mean (s) | SE | n |
| --- | --- | --- | --- |
| Vehicle | 183.90 | 11.23 | 8 |
| Example 1A - 1 mg/kg | 151.53 | 10.59 | 8 |
| Example 1A - 3 mg/kg | 172.02 | 13.05 | 8 |
| Imipramine 5 mg/kg | 161.94 | 13.54 | 8 |
| Example 1A - 1 mg/kg and imipramine 5 mg/kg | 90.93 | 12.35 | 8 |
| Example 1A - 3 mg/kg and imipramine 5 mg/kg | 67.98 | 8.47 | 8 |
| Imipramine 15 mg/kg | 61.70 | 11.20 | 8 |

The data from the second study evidences a potentiation effect of antidepressant-like activity when combination doses of Example 1A and imipramine are administered at doses not evidencing statistically significant activity when each compound is administered alone.

Prepulse Inhibition

Prepulse inhibition (PPI) of the acoustic startle reflex is used to evaluate sensory information-processing deficits observed in a number of neurologic and psychiatric conditions. Schizophrenic patients exhibit reduced sensory-motor gating, which is reflected in a reduced prepulse inhibition (PPI) of the startle reflex. This reduced inhibition can be ameliorated (reversed) by pharmaceutical antipsychotic agents. Certain pharmaceutical compounds that induce psychotic-like states (e.g., dopamine agonists, NMDA antagonists) also disrupt (suppress) PPI and antipsychotic pharmaceutical agents can reverse these deficits. PPI represents a mechanism for the gating or filtering out of irrelevant or distracting stimuli and is operationally defined as the reduction in startle response produced by a low-intensity stimulus presented before a high-intensity, startle-inducing stimulus.

Methods

Experiment 1

Reversal of (+)-(5α,7α,8β)-N-Methyl-N-[7-(1-Pyrrolidinyl)-1-Oxaspiro[4,5]dec-8-yl]-Benzeneacetamide (U69593, a selective K Opioid Receptor Agonist) Induced Disruption of PPI Sprague Dawley rats, 40 male, (Harlan, Indianapolis, Ind.), weighing approximately 250 grams and maintained on ad libitum food and water in the home cage, are divided into five groups of eight and dosed (per os) with vehicle, 0.1, 0.3 or 1.0 mg/kg compound of Example 1A one hour prior to testing. Each rat is dosed with either 3 mg/kg U-69593 (via subcutaneous injection) or vehicle fifteen minutes before testing.

Prepulse Inhibition Procedure: Following a 5 minute acclimation period, the first trial of a 40-trial session is initiated. The first five trials consist of 115 dB startle bursts, the remaining 35 trials were a pseudo-random combination of prepulse and startle trials. Prepulse trials consisted of a 115 dB sound burst preceded by a 65 dB prepulse of sound. Startle trials consisted of 115 dB sound bursts. In addition, there are five control trials where baseline response to the 60 dB background noise is assessed.

The intertrial interval (ITI) varied from 15 to 45 seconds and consisted of 60 dB background noise. Startle Amplitude for each trial is measured via accelerometer (Hamilton Kinder, model SM100RP) where average force in Newtons is recorded over a 120 millisecond period initiated upon presentation of the 40 millisecond, 115 dB startle stimulus for each trial.

Inhibition to startle reactivity is measured as each rat's percent change from mean prepulse startle reactivity to mean baseline startle reactivity. [(Mean Baseline Startle-Mean Prepulse Startle)/Mean Baseline Startle]×100.

Example 1A is prepared as a solution in a vehicle of sterile water with 85% lactic acid added dropwise until soluble and administered at 0.1, 0.3 and 1.0 mg/kg p.o. in a 1 ml/kg dose-volume.

U-69593 is prepared as a solution in a vehicle of sterile water and administered at 3.0 mg/kg subcutaneously in a 1 ml/kg dose-volume.

Data are analyzed using a One-Way ANOVA (Treatment), with Dunnett's Multiple Comparison Test to assess post hoc significance. Statistical analyses were performed in GraphPad Prism v.4.03.

Experiment 2

Reversal of Morphine Induced Disruption of PPI

Sprague Dawley rats, 56 male, (Harlan, Indianapolis, Ind.), weighing approximately 250 grams and maintained on ad libitum food and water in the home cage, are divided into four groups of 14 and dosed (per os) with either 10 mg/kg or 30 mg/kg Example 1A or vehicle one hour prior to testing and then dosed with either 20 mg/kg morphine (via subcutaneous injection) or vehicle fifteen minutes before testing.

The prepulse inhibition procedure and preparation of Example 1A are as described above.

Morphine is prepared as a solution in a vehicle of sterile water and administered at 20.0 mg/kg subcutaneously in a 1 ml/kg dose-volume.

Data are analyzed using a One-Way ANOVA (Treatment), with Dunnett's Multiple Comparison Test to assess post hoc significance. Statistical analyses are performed in GraphPad Prism v.4.03.

TABLE 7

PPI Results Experiment 2; Example 1A vs. Morphine

| | vehicle/ vehicle | vehicle/20 mg/kg morphine | 10 mg/kg Example 1A/20 mg/kg morphine | 30 mg/kg Example 1A/20 mg/kg morphine |
|---|---|---|---|---|
| % Inhibition | 62.49 | 4.72 | 18.66 | 57.12 |
| | 59.02 | 50.03 | 63.46 | 41.32 |
| | 61.78 | 26.99 | 42.77 | 30.93 |
| | 11.92 | −12.64 | 21.98 | 6.85 |
| | 15.96 | 34.65 | 40.70 | 16.56 |
| | 31.67 | 32.59 | 0.18 | 54.32 |
| | 63.33 | 5.49 | 21.00 | 18.94 |
| | 68.89 | 49.11 | 21.21 | 45.40 |
| | 61.08 | 53.95 | 50.34 | 42.78 |
| | 74.24 | 44.81 | 26.48 | 46.29 |
| | 53.15 | 35.01 | 18.04 | 39.26 |
| | 45.35 | −9.49 | 21.07 | 20.35 |
| | 57.72 | 51.85 | 29.49 | 40.02 |
| | 15.10 | 24.04 | 50.16 | 8.61 |

The data in Tables 6 and 7 evidence that the compound of Example 1A can reverse the sensory motor gating deficits induced by the Kappa agonist (U-69593; Table 6) and Mu agonist (morphine; Table 7) in rats. These data support the use of the compound of Example 1A in treating schizophrenia in patients.

We claim:

1. 3-Fluoro-4-[4-[2-(3,5-dimethylphenyl)pyrrolidin-1-yl-methyl]phenoxy]benzamide, or a pharmaceutically acceptable salt thereof.

2. (S)-3-Fluoro-4-[4-[2-(3,5-dimethylphenyl)pyrrolidin-1-yl-methyl]phenoxy]benzamide, or a pharmaceutically acceptable salt thereof.

3. A pharmaceutical composition comprising a compound of claim 1, or a pharmaceutically acceptable salt thereof, in association with a pharmaceutically acceptable carrier, diluent and/or excipient.

4. A pharmaceutical composition comprising a compound of claim 2, or a pharmaceutically acceptable salt thereof, in association with a pharmaceutically acceptable carrier, diluent and/or excipient.

5. A method of selectively antagonizing kappa opioid receptors in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

TABLE 6

PPI Results Experiment 1; Example 1A vs. U-69593

| | vehicle/ vehicle | vehicle/3.0 mg/kg U-69593 | 0.1 mg/kg Example 1A/ 3.0 mg/kg U-69593 | 0.3 mg/kg Example 1A/ 3.0 mg/kg U-69593 | 1.0 mg/kg Example 1A/3.0 mg/kg U-69593 |
|---|---|---|---|---|---|
| % Inhibition | 41.36 | 29.60 | 25.88 | 66.71 | 61.05 |
| | 68.63 | −24.89 | 31.40 | 71.91 | 59.31 |
| | 46.55 | −20.28 | 29.86 | 33.74 | 30.08 |
| | 71.55 | 43 | 55.18 | −1.75 | 52.23 |
| | 45.30 | −10.05 | 22.97 | 52.00 | 24.91 |
| | 48.43 | 3.47 | 54.62 | 47.01 | 70.96 |
| | 40.55 | 43.66 | 31.90 | 0.52 | 55.10 |
| | 62.72 | −3.46 | 9.79 | 42.14 | 71.68 |

6. A method of treating ethanol use disorder in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

7. A method of treating an anxiety disorder selected from panic disorder, obsessive-compulsive disorder, social phobia, generalized anxiety disorder, specific phobia, and posttraumatic stress disorder in a patient in need thereof which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

8. A method of treating an anxiety disorder selected from panic disorder, obsessive-compulsive disorder, social phobia, generalized anxiety disorder, specific phobia, and posttraumatic stress disorder; and ethanol use disorder in a patient in need thereof which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

9. A method of treating a depressive illness selected from major depression, dysthymia and bipolar disorder, in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

10. A method of treating a depressive illness selected from major depression, dysthymia and bipolar disorder, and ethanol use disorder in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

11. A method of treating an anxiety disorder selected from panic disorder, obsessive-compulsive disorder, social phobia, generalized anxiety disorder, specific phobia, and posttraumatic stress disorder, and a depressive illness selected from major depression, dysthymia and bipolar disorder in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

12. A method of treating an anxiety disorder selected from panic disorder, obsessive-compulsive disorder, social phobia, generalized anxiety disorder, specific phobia, and posttraumatic stress disorder; and a depressive illness selected from major depression, dysthymia and bipolar disorder; and ethanol use disorder in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

13. A method of treating schizophrenia in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

14. A method of treating schizophrenia and ethanol use disorder in a patient in need thereof, which comprises administering a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, to said patient.

15. A pharmaceutical composition comprising a therapeutically effective amount of (S)-3-fluoro-4-[4-[2-(3,5-dimethylphenyl)pyrrolidin-1-yl-methyl]phenoxy]benzamide, or a pharmaceutically acceptable salt thereof, and a therapeutically effective amount of a tertiary amine tricyclic norepinephrine reuptake inhibitor selected from amitriptyline, clomipramine, doxepin, imipramine and (+)-trimipramine, or a pharmaceutically acceptable salt thereof, in association with a pharmaceutically acceptable carrier, diluent and/or excipient.

16. A method of treating ethanol use disorder and a depressive illness selected from major depression, dysthymia and bipolar disorder, in a patient in need thereof which comprises administering (S)-3-fluoro-4-[4-[2-(3,5-dimethylphenyl)pyrrolidin-1-yl-methyl]phenoxy]benzamide, or a pharmaceutically acceptable salt thereof, and a tertiary amine tricyclic norepinephrine reuptake inhibitor selected from amitriptyline, clomipramine, doxepin, imipramine and (+)-trimipramine, or a pharmaceutically acceptable salt thereof, to said patient.

* * * * *

UNITED STATES PATENT AND TRADEMARK OFFICE
CERTIFICATE OF CORRECTION

PATENT NO. : 7,709,522 B2  Page 1 of 1
APPLICATION NO. : 12/352869
DATED : May 4, 2010
INVENTOR(S) : Nuria Diaz Buezo et al.

It is certified that error appears in the above-identified patent and that said Letters Patent is hereby corrected as shown below:

On the Title Page:
Insert Item --(60) Related U.S. Application Data
Provisional Application No. 61/039,121, filed March 25, 2008--.

On the Title Page, under Item (30) Foreign Application Priority Data
replace "(ES)" with --(EP)--.

Col. 1 lines 3-4, insert the following cross-reference after the title:
--This application claims the benefit of US provisional application no. 61/039,121 filed March 25, 2008 and EP application no. 08380012.8, filed January 22, 2008.--.

Signed and Sealed this

Sixteenth Day of November, 2010

David J. Kappos
*Director of the United States Patent and Trademark Office*